| United States Patent [19] | [11] Patent Number: 4,800,204 |
| --- | --- |
| Mueller | [45] Date of Patent: Jan. 24, 1989 |

[54] METHOD OF CONTROLLING TOBACCO USE

[76] Inventor: Peter S. Mueller, 182 Snowden La., Princeton, N.J. 08540

[21] Appl. No.: 190,428

[22] Filed: May 5, 1988

Related U.S. Application Data

[63] Continuation of Ser. No. 47,753, May 7, 1987, abandoned.

[51] Int. Cl.$^4$ .......................................... A61K 31/505
[52] U.S. Cl. .................................. 514/267; 514/268; 514/813
[58] Field of Search ...................... 514/267, 268, 813

[56] References Cited

PUBLICATIONS

Imperato et al., European J. of Pharm., 132 (1986) 337–338.

*Primary Examiner*—Stanley J. Friedman
*Attorney, Agent, or Firm*—Gerald D. Sharkin; Robert S. Honor; Thomas O. McGovern

[57] ABSTRACT

The control of tobacco use in humans with a direct dopamine receptor agonist.

18 Claims, No Drawings

METHOD OF CONTROLLING TOBACCO USE

This is a continuation of application Ser. No. 047,753, filed May 7, 1987, now abandoned.

This invention relates to a new method of controlling tobacco use. More particularly, it relates to a method of reducing or eliminating tobacco consumption in humans and to a method of preventing the craving which arises when a tobacco user attempts to cut down on tobacco use or stop it completely.

Tobacco use and smoking in particular has become recognized over the last few decades as a major medical and social problem. This includes not only cigarette smoking, but also cigar and pipe smoking and smokeless tobacco use including chewing tobacco and snuff. Because of the medical problems associated with its use, the majority of tobacco users would like to stop or at least reduce the amount of tobacco consumed each day. In addition to the medical problems, there are also restrictions now relating to smoking in the work place and in public areas, such as restaurants and shopping centers, which also require smokers to exercise considerably greater control over their smoking habits. However, many people find it virtually impossible, especially in the case of cigarettes, to control their tobacco habit. Where a person, for example, has stopped smoking cigarettes completely, there is oftentimes a continuous craving, and if that person tries to alleviate the craving by smoking even just one cigarette, he or she very quickly returns to his or her original level of consumption. Similarly, if one tries to cut down on the amount of tobacco used, such as the number of cigarettes smoked each day, the craving increases in intensity, and the smoker soon returns to the former level of use. Prior to this invention, tobacco users, especially smokers, had to rely on will power and complete abstention to manage their tobacco habit. There was no known drug which permitted the users to control effectively their craving or use of tobacco.

In the present invention, it has been found that tobacco use, in particular smoking, especially cigarette smoking, can be controlled by administering to a human tobacco user a long-acting direct dopamine receptor agonist in an amount which is effective in reducing or eliminating the craving for tobacco when cutting down on smoking or stopping completely. Direct dopamine receptor agonists stimulate postsynaptic dopamine receptors in contrast to agonists which act presynaptically and are active only where there are functioning dopaminergic neurons. The dopamine agonist can be any direct dopamine stimulating agent, such as, bromocriptine, pergolide, lisuride and lergotrile, to name a few. The preferred dopamine agonist of the invention is bromocriptine. The amount of agonist administered will vary depending on the active agent used and the individual undergoing treatment. It has been found, however, that good results are obtained in the majority of cases with daily dosages in the lowest range utilized for the agonists' known indications. Bromocriptine is generally administered in individual dosages ranging from 0.5 to 10 milligrams per day. Pergolide and lisuride are effective at daily doses of about 0.05 to 1.0 milligram. Generally, the daily dosage for the ergot alkaloid type dopamine agonist for the tobacco indication will be from about 0.05 to, in some cases, about 50 milligrams per day. Normally, at least 0.5 milligram of the agonist is administered daily for the use; and in most cases, it is not necessary to exceed 20 milligrams a day. The agonist is usually administered on a set schedule, for example, every 4 to 6 hours, or it can be administered as needed to control tobacco use. It can also be administered once a day in a controlled release form. Generally, the preferred agonist, bromocriptine, is administered at doses of from about 0.5 to 15 milligrams per day, although higher doses may be required by some individuals to control their tobacco habit. In most cases, however, it is administered in unit doses of about 0.5 to 2.5 milligrams 2 to 4 times daily, preferably 2.5 milligrams 3 times daily conveniently at mealtime. Normally, the initial dose of bromocriptine is about 0.5 to 1, preferably about 0.625 milligrams, 3 times a day for one week; then about 1 to 2, preferably 1.25, milligrams 3 times a day for the second week; and from then on, about 2 to 4, preferably 2.5, milligrams 3 times a day or as needed. It will be appreciated that such doses are lower than those administered for the known indications of this drug, which can range from about 7.5 to about 50 milligrams daily.

When appropriate, the dopamine agonist used in the invention may be employed in free base form or in pharmaceutically acceptable salt form. The various ergot derivatives referred to above may, for example, be used in the form of the mesylate or hydrochloride salt. Generally, the activities of such salt forms will be of the same order as that of the corresponding free base form, and references to compounds in the free base form throughout the specification and claims are to be understood as including known salt forms.

The active ingredient of the invention may be administered orally or parenterally as such or admixed with conventional pharmaceutical carriers. They may be administered orally in such forms as tablets, dispersible powders, granules, capsules, syrups and elixirs, or parenterally as solutions, e.g., a sterile injectable aqueous solution. Tablets may contain the active ingredients in admixture with conventional pharmaceutically acceptable excipients, e.g., inert diluents and granulating, disintegrating and lubricating agents. The tablets or the active ingredient may be uncoated or coated by known techniques to delay disintegration and absorption in the gastrointestinal tract and thereby provide a sustained action over a longer period. Similarly, suspensions, syrups and elixirs may contain the active ingredients in admixture with any of the conventional excipients utilized in the preparation of such compositions. Capsules may contain the active ingredients alone or admixed with an inert solid diluent. The injectable compositions are formulated as known in the art. These pharmaceutical preparations may contain up to about 90% of the active ingredients in combination with the carrier or adjuvant.

Pharmaceutical compositions containing the most preferred compound, bromocriptine mesylate, at dosages of 2.5 and 5 milligrams and suitable for oral administration in accordance with the method of the invention are commercially available. The tablet form is readily broken in half or into quarters for administration of lower doses. Preferably the 2.5 milligram form is administered 3 times a day at meal time. Alternatively, a unit dosage in delayed release form containing equivalent dosages, e.g. 10 milligrams, may be employed.

The following examples illustrate the invention.

EXAMPLE 1

A 55-year-old female, married and a professional, smoked 1 to 2 packs of cigarettes a day since the age of 15. She smoked approximately 1 pack a day for about 20 years and gradually increased to 2 packs a day for the last 20 years. She began taking 2.5 milligrams of bromocriptine twice a day on an irregular basis, gradually increasing to 2.5 milligrams 3 times a day. After approximately two months, she decided that she wanted to stop smoking completely and found that she was able to do so without the usual craving. She subsequently found that she was able to smoke socially at parties and professional functions without returning to her former level of consumption. At the present time, she estimates that she smokes at most approximately 3 packs of cigarettes a year.

EXAMPLE 2

A 42-year-old male construction worker began smoking at the age of 14; and for approximately 28 years, he consumed 1 pack of cigarettes a day. At one point, he stopped smoking for about two months, but began smoking again and was quickly back to 1 pack a day. He began taking 2.5 milligrams of bromocriptine 3 times a day; and for six months, he was able to reduce his smoking to 7 cigarettes a day. At this point, he stopped taking bromocriptine and began taking the central stimulant, methylphenidate, which has presynaptic dopamine receptor activity. Within a very short period of time, he was back to 1 pack of cigarettes a day. The direct dopamine receptor agonist, bromocriptine, reduced craving and allowed this individual to control his smoking. The presynaptic dopamine receptor agonist, on the other hand, permitted cigarette craving to return to normal; and eventually the man returned to his original level of consumption.

EXAMPLE 3

A 43-year-old female began smoking at the age of 17 and smoked about one-half pack of cigarettes a day for approximately 24 years. At one time, she stopped smoking for about 2 years but eventually returned to her former level of use. She began taking 2.5 milligrams of bromocriptine 3 times a day and soon completely stopped smoking. As in the Example 1 case above, she subsequently found that she could smoke socially without returning to her former level of consumption. She now smokes 1 or 2 cigarettes one or twice a year.

EXAMPLE 4

A 50-year-old female began smoking cigarettes at the age of 16 and smoked one-half pack a day until she was 27. She gradually increased her consumption to one pack a day. At age 44, she stopped smoking completely for 6 months. She started smoking again; and by age 45, she was smoking one and a half packs a day. Her doctor put her on 2.5 milligrams of bromocriptine 3 times a day; and her smoking dropped to less than one-half pack a day. She experienced no craving or any great need to smoke. The doctor then took her off bromocriptine and put her on methylphenidate. Within a very short period of time, her consumption was back up to one and a half packs of cigarettes a day.

EXAMPLE 5

For 10½ years, a 30-year-old man had consumed each month about 25 cans of a commercial snuff product containing approximately 1.2 oz. per can. This was administered by inserting a small amount of the snuff between his gum and cheek. On various occasions, he tried to give up the habit by stopping in the morning. However, by the afternoon, the craving for snuff and the withdrawal symptoms, including sweating and anxiety, became intolerable. He started taking 2.5 milligrams of bromocriptine three times a day; and within one week, he completely stopped using the product. There were no withdrawal symptoms; and he has not experienced a craving for smokeless tobacco, since he stopped.

I claim:

1. A method of controlling tobacco use in a human tobacco user who desires to reduce or stop tobacco use, which comprises administering to the user a pharmaceutically acceptable direct dopamine receptor agonist in an amount effective to control tobacco use.

2. A method according to claim 1 of controlling cigarette consumption in a human who desires to reduce or stop cigarette smoking, which comprises administering to the human a pharmaceutically acceptable direct dopamine receptor agonist in an amount effective to control cigarette smoking.

3. A method of reducing cigarette smoking according to claim 2.

4. A method of stopping cigarette smoking according to claim 2.

5. A method of reducing or stopping cigar smoking according to claim 1.

6. A method of reducing or stopping pipe smoking according to claim 1.

7. A method of reducing or stopping the use of smokeless tobacco according to claim 1.

8. A method of reducing or stopping the use of chewing tobacco according to claim 7.

9. A method of reducing or stopping the use of snuff according to claim 7.

10. A method according to claim 1 in which the dopamine agonist is selected from bromocriptine, pergolide, lisuride or lergotrile.

11. A method according to claim 1 in which the dopamine agonist is bromocriptine in free base form or in pharmaceutically acceptable acid addition salt form.

12. A method according to claim 11 in which 0.5 to 15 milligrams of bromocriptine are administered daily in free base form or in pharmaceutically acceptable acid addition salt form.

13. A method according to claim 11 in which 0.5 to 2.5 milligrams of bromocriptine per unit dose in free base form or in pharmaceutically acceptable acid addition salt form are administered three times daily.

14. A method according to claim 4 in which 2.5 milligrams of bromocriptine per unit dose in free base form or in pharmaceutically acceptable acid addition salt form are administered three times daily.

15. A method of controlling tobacco use in a human tobacco user who desires to reduce or stop tobacco use, which comprises administering to the user a pharmaceutically acceptable ergot alkaloid direct dopamine receptor agonist in an amount effective to control tobacco use.

16. A method according to claim 15 of controlling cigarette consumption in a human who desires to reduce or stop cigarette smoking, which comprises administering to the human a pharmaceutically acceptable ergot alkaloid direct dopamine receptor agonist in an amount effective to control cigarette smoking.

17. A method according to claim 15 in which about 0.05 to about 50 milligrams of the agonist are administered daily.

18. A method according to claim 15 in which about 0.05 to about 20 milligrams of the agonist are administered daily.

* * * * *